(12) United States Patent
Honda et al.

(10) Patent No.: US 10,441,341 B2
(45) Date of Patent: Oct. 15, 2019

(54) TREATMENT SYSTEM AND ACTUATION METHOD FOR TREATMENT SYSTEM

(71) Applicant: OLYMPUS CORPORATION, Tokyo (JP)

(72) Inventors: Yoshitaka Honda, Hachioji (JP); Kazue Tanaka, Sagamihara (JP); Takashi Irisawa, Hachioji (JP); Sadayoshi Takami, Hachioji (JP)

(73) Assignee: Olympus Corporation, Tokyo (JP)

( * ) Notice: Subject to any disclaimer, the term of this patent is extended or adjusted under 35 U.S.C. 154(b) by 756 days.

(21) Appl. No.: 14/809,486

(22) Filed: Jul. 27, 2015

(65) Prior Publication Data

US 2015/0327916 A1 Nov. 19, 2015

Related U.S. Application Data

(63) Continuation of application No. 13/921,603, filed on Jun. 19, 2013, now Pat. No. 9,119,619, which is a
(Continued)

(51) Int. Cl.
*A61B 18/08* (2006.01)
*A61B 18/10* (2006.01)
(Continued)

(52) U.S. Cl.
CPC ............ *A61B 18/085* (2013.01); *A61B 18/10* (2013.01); *A61B 18/1206* (2013.01);
(Continued)

(58) Field of Classification Search
CPC ........... A61B 2018/00589; A61B 2018/00595; A61B 2018/0063; A61B 2018/00666;
(Continued)

(56) References Cited

U.S. PATENT DOCUMENTS 6,216,703 B1 4/2001 Manker et al.
6,287,304 B1 9/2001 Eggers et al.
(Continued)

FOREIGN PATENT DOCUMENTS

EP 2106762 A1 10/2009
JP 2009247893 A 10/2009
(Continued)

OTHER PUBLICATIONS

International Search Report dated Feb. 19, 2013 received in International Application No. PCT/JP2012/079373.
(Continued)

*Primary Examiner* — Jaymi E Della
*Assistant Examiner* — Sean W Collins
(74) *Attorney, Agent, or Firm* — Scully Scott Murphy & Presser, P.C.

(57) ABSTRACT

A treatment system includes a power source for heat generation which outputs power for heat generation, a grasping member having a heating element which applies the power for heat generation as thermal energy to a grasped living tissue and is disposed at a grasping surface, and a control section which repeats a first control mode of performing control such that the heating element reaches a first temperature and a second control mode of performing control such that the heating element becomes lower than the first temperature, and controls the power source for heat generation according to a temperature change parameter based on change in temperature of the heating element in the first control mode or the second control mode so as to end application of the thermal energy.

13 Claims, 10 Drawing Sheets

Related U.S. Application Data continuation of application No. PCT/JP2012/079373, filed on Nov. 13, 2012.

(60) Provisional application No. 61/569,336, filed on Dec. 12, 2011.

(51) Int. Cl.

| | | |
|---|---|---|
| *A61B 18/12* | (2006.01) | |
| *A61B 18/14* | (2006.01) | |
| *A61B 18/00* | (2006.01) | |

(52) U.S. Cl.
CPC ...... *A61B 18/1442* (2013.01); *A61B 18/1445* (2013.01); *A61B 2018/00642* (2013.01); *A61B 2018/00654* (2013.01); *A61B 2018/00702* (2013.01); *A61B 2018/00714* (2013.01); *A61B 2018/00791* (2013.01); *A61B 2018/00875* (2013.01); *A61B 2018/00886* (2013.01); *A61B 2018/00994* (2013.01); *A61B 2018/1273* (2013.01); *A61B 2018/146* (2013.01)

(58) Field of Classification Search
CPC ........... A61B 2018/00708; A61B 2018/00714; A61B 18/085; A61B 18/10; A61B 18/1206; A61B 18/1442; A61B 18/1445; A61B 2018/146; A61B 2018/00642; A61B 2018/00654; A61B 2018/00886; A61B 2018/00994; A61B 2018/1273; A61B 2018/00791; A61B 2018/00702; A61B 2018/00875
USPC ................................... 606/50–52, 31, 38, 42
See application file for complete search history.

(56) References Cited

U.S. PATENT DOCUMENTS

| | | |
|---|---|---|
| 8,632,531 B2 | 1/2014 | Bouthillier et al. |
| 2002/0082593 A1 | 6/2002 | Hareyama et al. |
| 2003/0073987 A1 | 4/2003 | Sakurai et al. |
| 2003/0171747 A1 | 9/2003 | Kanehira et al. |
| 2003/0212394 A1* | 11/2003 | Pearson ............. A61B 18/1477 606/41 |
| 2004/0010289 A1* | 1/2004 | Biggs ....................... A61N 1/06 607/2 |
| 2004/0092923 A1 | 5/2004 | Miura et al. |
| 2005/0022560 A1 | 2/2005 | Rowe et al. |
| 2005/0222560 A1 | 10/2005 | Kimura et al. |
| 2008/0015575 A1 | 1/2008 | Odom et al. |
| 2008/0228181 A1* | 9/2008 | Godara ............. A61B 18/1206 606/34 |
| 2009/0076506 A1 | 3/2009 | Baker |
| 2009/0248002 A1 | 10/2009 | Takashino et al. |
| 2010/0185196 A1 | 7/2010 | Sakao et al. |
| 2011/0077629 A1 | 3/2011 | Tanaka et al. |
| 2011/0077630 A1 | 3/2011 | Tanaka et al. |
| 2012/0022517 A1* | 1/2012 | Stuebe ................ A61B 18/085 606/31 |
| 2012/0265194 A1* | 10/2012 | Podhajsky ......... A61B 18/1206 606/34 |

FOREIGN PATENT DOCUMENTS

| | | |
|---|---|---|
| JP | 2010538796 A | 12/2010 |
| JP | 2011194059 A | 10/2011 |
| WO | 2009039179 A1 | 3/2009 |

OTHER PUBLICATIONS

Extended European Search Report dated Jan. 9, 2015 received in Application No. PCT/JP2012079373.
U.S. Office Action dated Dec. 30, 2014 received in corresponding U.S. Appl. No. 13/921,603.

* cited by examiner

TREATMENT SYSTEM AND ACTUATION METHOD FOR TREATMENT SYSTEM

CROSS REFERENCE TO RELATED APPLICATION

This application is a continuation application of U.S. patent application Ser. No. 13/921,603 filed on Jun. 19, 2013, which is a continuation application of PCT/JP2012/079373 filed on Nov. 13, 2012 and claims benefit of U.S. Provisional Patent Application No. 61/569,336 filed in the U.S.A. on Dec. 12, 2011, the entire contents of each of which are incorporated herein by reference.

BACKGROUND OF THE INVENTION

1. Field of the Invention

Embodiments of the present invention relate to a treatment system including one pair of grasping members which apply thermal energy to a grasped living tissue and an actuation method for the treatment system.

2. Description of the Related Art

U.S. Patent Application Publication No. 2009/076506 discloses a treatment system including one pair of grasping members which apply high-frequency power energy and thermal energy to a grasped living tissue, a high-frequency power source which outputs high-frequency power for applying high-frequency power energy, a power source for heat generation which outputs power for heat generation for applying thermal energy, and a control section which controls the high-frequency power source and the power source for heat generation for switching between application of high-frequency power energy and application of thermal energy.

U.S. Patent Application Publication No. 2009/0248002 discloses a treatment system which first applies high-frequency power energy to a living tissue and then starts application of thermal energy. High-frequency power energy acts to release intracellular components including polymer compounds typified by protein by destroying cell membranes in a living tissue and make the intracellular components uniformed with extracellular components typified by collagen. Such uniforming of a living tissue promotes joining of a living tissue through subsequent application of thermal energy.

For application of thermal energy, a process is known of raising temperature of a heating element to a predetermined temperature on the basis of a sensed temperature and then performing constant temperature control so as to hold the temperature at the predetermined temperature.

U.S. Patent Application Publication No. 2005/0222560 discloses a treatment instrument which performs temperature control by intermittently applying thermal energy, i.e., outputting power for heat generation.

SUMMARY OF THE INVENTION

A treatment system according to an embodiment includes a high-frequency power source which outputs high-frequency power, a power source for heat generation which outputs power for heat generation, one pair of grasping members having one pair of electric conductors which apply the high-frequency power as high-frequency power energy to a grasped living tissue and are disposed at respective grasping surfaces of the two grasping members and a heating element which applies the power for heat generation as thermal energy to the living tissue, is disposed at at least one of the grasping members, and is made of a material having a positive temperature coefficient of resistance, and a control section which controls the high-frequency power source and the power source for heat generation after application of the high-frequency power energy ends so as to start application of the thermal energy, and repeats a first control mode of performing control such that the heating element reaches a first temperature and a second control mode of performing control such that the heating element becomes lower than the first temperature, and controls the power source for heat generation according to a temperature change parameter based on change in temperature of the heating element in the first control mode or the second control mode so as to end application of the thermal energy, after application of the thermal energy starts.

An actuation method for a treatment system according to another embodiment includes a step of setting a treatment condition for the treatment system including one pair of grasping members which apply high-frequency power energy and thermal energy to a grasped living tissue, a high-frequency power source which outputs high-frequency power for applying the high-frequency power energy, and a power source for heat generation which outputs power for heat generation for applying the thermal energy, a step of controlling the high-frequency power source on the basis of the treatment condition and applying the high-frequency power energy to the living tissue, a step of acquiring a temperature change parameter, on the basis of change in temperature of the heating element in a first control mode of performing control such that the heating element reaches a first temperature or a second control mode of performing control such that the heating element becomes lower than the first temperature, during application of the thermal energy by repeating the first control mode and the second control mode on the basis of the treatment condition after application of the high-frequency power energy is ended on the basis of the treatment condition, and a step of ending application of the thermal energy according to the temperature change parameter.

A treatment system according to yet another embodiment includes a power source; a control section configured to control the power source; and a treatment instrument including a pair of grasping members configured to grasp a living tissue, and a heating element disposed at at least one of the pair of the grasping members, the heating element being electrically connected to the power source and configured to generate heat with power outputted from the power source; wherein the control section is configured to repeatedly perform a control in a first control mode for controlling an output of the power such that a temperature of the heating element rises and a control in a second control mode for controlling the output of the power such that the temperature of the heating element decreases, and perform a control to stop the output of the power when a time period for the temperature of the heating element to reach a predetermined temperature is shorter than a preset threshold time period, or when a rate of change in the temperature of the heating element is faster than a preset threshold rate.

DETAILED DESCRIPTION OF THE PREFERRED EMBODIMENTS

First Embodiment

<Configuration of Treatment System>

Figure 1:
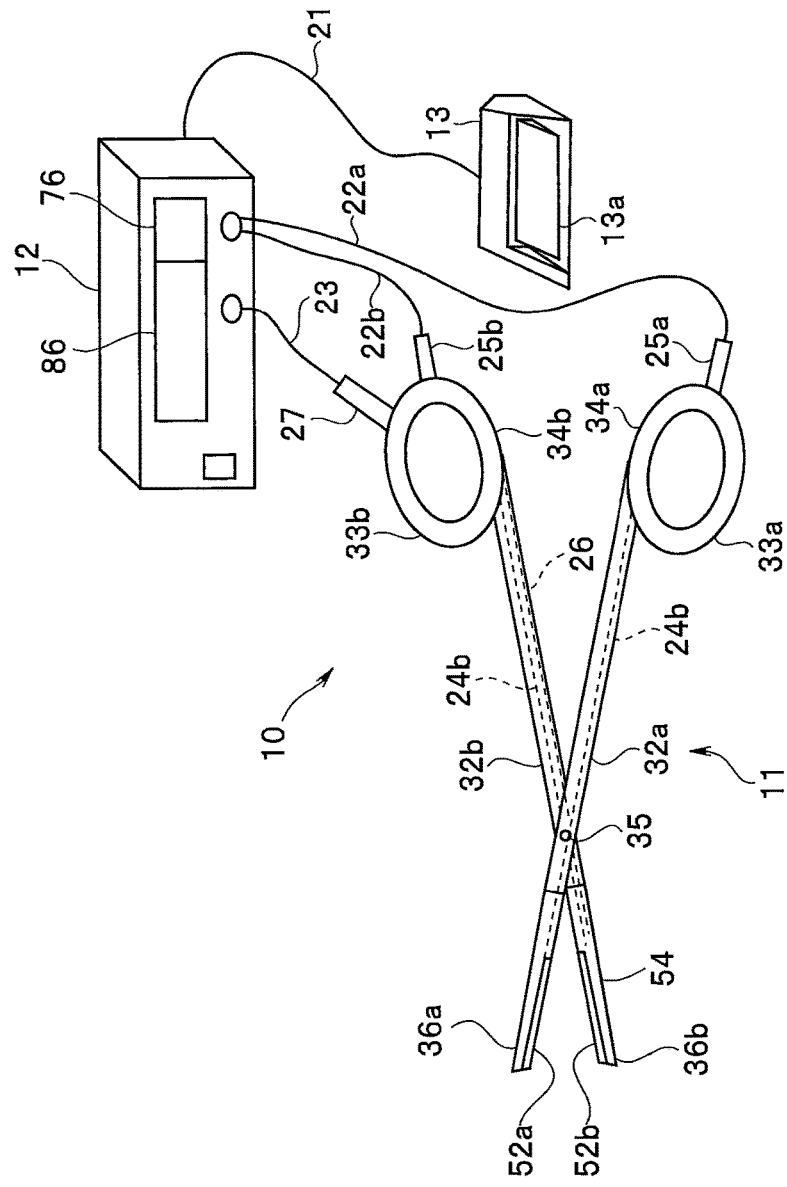
FIG. 1 is an external view of a treatment system according to a first embodiment.

A treatment system 10 according to a first embodiment will first be described. As shown in FIG. 1, the treatment system 10 includes a treatment instrument 11, a power supply portion 12, and a foot switch 13. The treatment system 10 switches between high-frequency power energy and thermal energy and applies, using the power supply portion 12, the energy to a living tissue grasped by jaws 36a and 36b which are one pair of grasping members of the treatment instrument 11. Note that high-frequency power and power for heat generation may hereinafter be abbreviated as "HF" and "TH," respectively. For example, high-frequency power energy is referred to as HF energy.

The treatment instrument 11 is connected to the power supply portion 12 by HF lines 22a and 22b and a TH line 23. Note that although the HF lines 22a and 22b, the TH line 23, and the like each have two pieces of wiring, the two pieces of wiring are expressed as one line. The foot switch 13 is connected to the power supply portion 12 by a switch line 21.

The treatment instrument 11 has one pair of scissors constituent members 32a and 32b, one pair of handle portions 34a and 34b, and the one pair of jaws 36a and 36b. The handle portions 34a and 34b are provided at proximal end portions of the scissors constituent members 32a and 32b. The handle portions 34a and 34b are operated while being held in a hand by a surgeon. The jaws 36a and 36b are provided at distal end portions of the scissors constituent members 32a and 32b to grasp a living tissue to be treated.

The scissors constituent members 32a and 32b are placed one on the other so as to substantially intersect each other between distal ends and proximal ends of the scissors constituent members 32a and 32b. A fulcrum pin 35 which pivotably couples the scissors constituent members 32a and 32b is provided at an intersection portion of the scissors constituent members 32a and 32b.

The handle portions 34a and 34b are provided with rings 33a and 33b on which a surgeon puts his or her fingers. When the surgeon puts a thumb and a middle finger through the rings 33a and 33b, respectively, and opens and closes the rings 33a and 33b, the jaws 36a and 36b open and close in tandem with the motion.

Respective energy release elements which apply energy to a grasped living tissue are disposed at the jaws 36a and 36b. That is, an electrode 52a as the energy release element which has a grasping surface and is made of an electric conductor is disposed at the jaw 36a. An electrode 52b as the energy release element which has a grasping surface and is made of an electric conductor and a heater member 53 as a heating element are disposed at the jaw 36b. The heater member 53 is embedded in the jaw 36b while the heater member 53 is disposed on a reverse surface of the electrode 52b that is made of a high thermal conductor.

Figure 2:
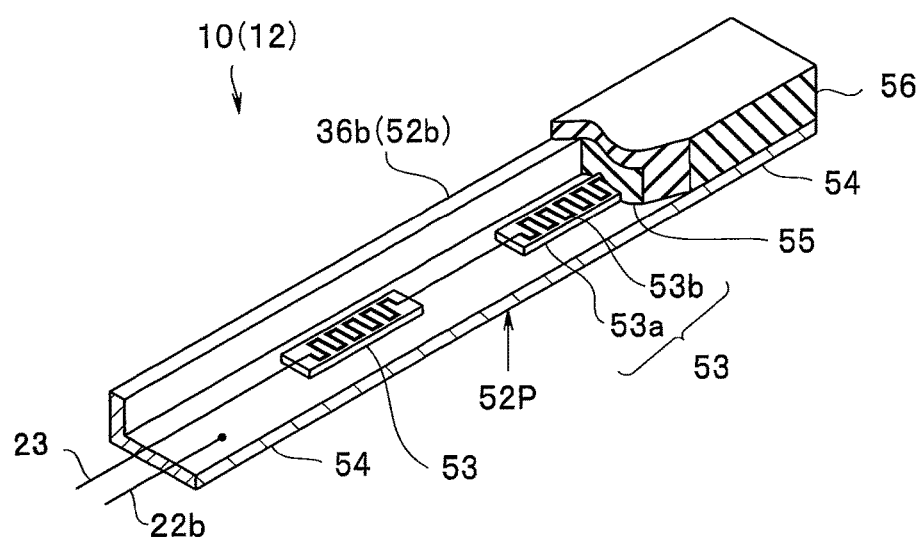
FIG. 2 is a three-dimensional cross-sectional view for explaining a structure of a jaw in the treatment system according to the first embodiment.

That is, as shown in FIG. 2, in the jaw 36b of the treatment instrument 11, the heater member 53 is joined to a surface reverse to a grasping surface 52P of a base 54 which is made of copper. The heater member 53 is covered with a sealing member 55 and a cover member 56. Note that FIG. 2 shows a portion of the jaw 36b and that three or more heater members 53 may be joined to each jaw 36b.

In the heater member 53, a thin-film resistor or a thick-film resistor is disposed as a heating pattern 53b on a substrate 53a of, e.g., alumina or aluminum nitride. The thin-film resistor is made of, e.g., an electrically conductive thin film which is formed by a thin film formation method, such as PVD (physical vapor deposition) or CVD (chemical vapor deposition), or foil of an electrically conductive metal, such as SUS. The thick-film resistor is formed by a thick film formation method, such as screen printing. The heating pattern 53b is formed of a refractory metal material, such as molybdenum, which exhibits a positive temperature coefficient of resistance indicating that electric resistance increases directly with temperature.

Note that the heater member 53 may also be disposed at the jaw 36a of the treatment instrument 11. That is, a heating element only needs to be disposed at at least one grasping member.

HF lines 24a and 24b for supplying HF to the electrodes 52a and 52b are disposed inside the scissors constituent members 32a and 32b, respectively. The HF lines 24a and 24b extend from the jaws 36a and 36b to the handle portions 34a and 34b, respectively. HF terminals 25a and 25b are provided at the rings 33a and 33b, respectively. The HF terminals 25a and 25b are connected to the HF lines 24a and 24b, respectively. For the reason, when HF is supplied to the electrodes 52a and 52b while a living tissue is grasped by the jaws 36a and 36b, HF is passed through the living tissue between the electrodes 52a and 52b. In other words, HF energy is applied to the living tissue.

A TH line 26 for supplying TH to the heater member 53 is disposed inside the scissors constituent member 32b. The TH line 26 extends from the jaw 36b to the handle portion 34b. A TH terminal 27 which is connected to the TH line 26 is provided at the ring 33b. For the reason, when TH is supplied to the heater member 53 through the TH line 26, the heater member 53 generates heat. That is, the TH is converted into thermal energy by the heater member 53, the thermal energy is transferred to the electrode 52b, and the thermal energy is applied to a living tissue in contact with the grasping surface of the electrode 52b.

As described above, when HF is passed between the electrodes 52a and 52b, the treatment instrument 11 applies HF energy to a living tissue grasped between the jaws 36a and 36b. When TH is passed through the heater member 53 in the treatment instrument 11, the TH is converted into the thermal energy. The treatment instrument 11 applies the thermal energy to the living tissue.

The foot switch 13 has a pedal 13a. While the pedal 13a is pressed, the power supply portion 12 outputs HF or TH on the basis of a setting state (a state in which an output value, output timing, and the like are controlled). When the press of the pedal 13a is canceled, the power supply portion 12 forcibly stops outputting the power.

Figure 3:
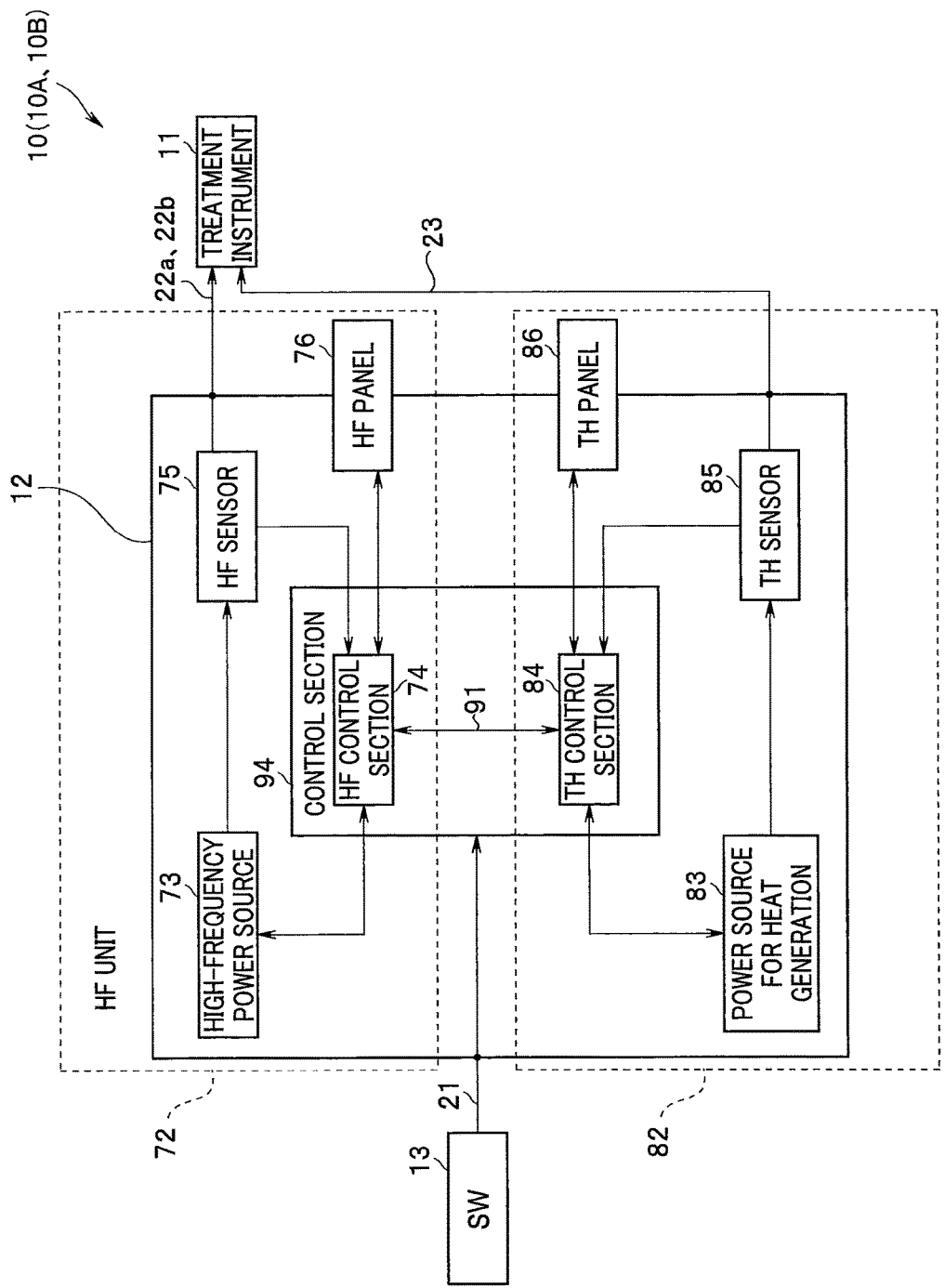
FIG. 3 is a configuration diagram of the treatment system according to the first embodiment.

As shown in FIG. 3, the power supply portion 12 is composed of an HF unit 72 and a TH unit 82. The HF unit 72 has a high-frequency power source 73 which outputs HF, an HF control section 74 which controls the high-frequency power source 73 and is made up of a semiconductor circuit, such as a CPU, and the like, an HF sensor 75 which is a high-frequency power measuring section which measures voltage and current of HF outputted by the high-frequency power source 73, and an operation panel 76.

The TH unit 82 has a power source 83 for heat generation which outputs TH, a TH control section 84 which controls the power source 83 for heat generation and is made up of a semiconductor circuit, such as a CPU, and the like, a TH sensor 85 which is a heat generation power measuring section that measures voltage and current of TH outputted by the power source 83 for heat generation, and an operation panel 86.

The HF control section 74 and the TH control section 84 are connected by a communication line 91 which can transmit a signal in both directions to constitute a control section 94. That is, the control section 94 controls the high-frequency power source 73 and the power source 83 for heat generation. The operation panels 76 and 86 each have a setting function portion, with which a surgeon sets a treatment condition, and a display function of displaying a treatment status.

The HF sensor 75 is connected to the treatment instrument 11 via the HF lines 22a and 22b. The high-frequency power source 73 and the HF sensor 75 are connected to the HF control section 74. The HF control section 74 is further connected to the operation panel 76. The HF control section 74 calculates HF information, such as power and impedance, on the basis of information from the HF sensor 75, sends a control signal to the high-frequency power source 73, and sends information to be displayed to the operation panel 76. HF outputted by the high-frequency power source 73 that is controlled by the HF control section 74 is transmitted to the electrodes 52a and 52b of the treatment instrument 11.

The TH control section 84 calculates temperature of the heater member 53 as TH information on the basis of information from the TH sensor 85, in addition to power, a resistance value, and the like. That is, since the heating pattern of the heater member 53 is made of a material having a positive temperature coefficient of resistance, as already described, the TH control section 84 can calculate the temperature of the heater member 53 from a TH resistance value which is calculated from voltage and current of TH. The TH control section 84 sends a control signal to the power source 83 for heat generation on the basis of the TH information. TH outputted by the power source 83 for heat generation that is controlled by the TH control section 84 is transmitted to the heater member 53 of the treatment instrument 11.

Note that the HF control section 74 also sends a control signal to the TH control section 84 at the end of application of HF such that the TH control section 84 starts outputting TH.

As described above, the treatment instrument 11 has a function of a bipolar-type high-frequency treatment instrument and a function of a treatment instrument for heat generation.

Figure 4:
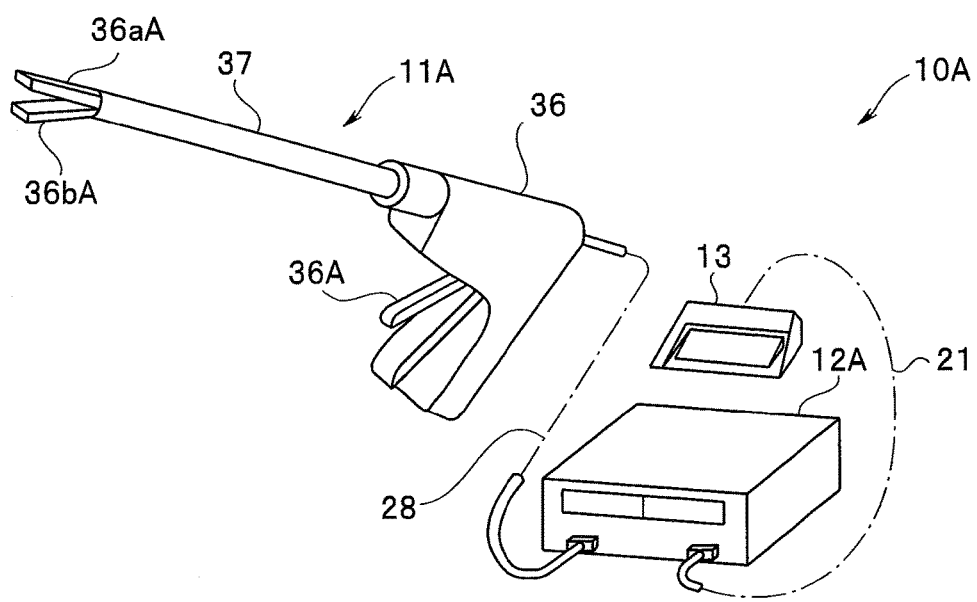
FIG. 4 is an external view of a treatment system according to a modification of the first embodiment.

Note that the treatment instrument of the treatment system according to the embodiment may be a so-called linear-type treatment instrument. For example, a treatment system 10A according to a modification shown in FIG. 4 includes a linear-type treatment instrument 11A, a power supply portion 12A, and the foot switch 13.

The treatment instrument 11A has a handle 36, a shaft 37, and one pair of jaws 36aA and 36bA which are grasping members that grasp a living tissue. Structures of the jaws 36aA and 36bA are identical to the structures of the jaws 36a and 36b.

The handle 36 has a shape which is easy for a surgeon to grip, such as a substantially L-shape. The handle 36 has an open/close knob 36A. The open/close knob 36A is designed such that the jaws 36a and 36b grasp a living tissue when a surgeon presses and operates the open/close knob 36A. HF electrodes (not shown) and heater members (not shown) of the jaws 36aA and 36bA are connected to the power supply portion 12A via a piece 28 of wiring. That is, the piece 28 of wiring is made up of the HF lines 22a and 22b and the TH line 23. A basic configuration and a function of the power supply portion 12A are identical to the basic configuration and the function of the power supply portion 12.

That is, any of treatment instruments having various structures can be used as long as the treatment instrument can apply high-frequency power energy and thermal energy to a grasped living tissue.

<Motion of Treatment System>

An actuation method for the treatment system 10 will be described.

The treatment system 10 first applies HF energy to a grasped living tissue and applies thermal energy after the application of HF energy ends. In other words, the control section 94 controls the high-frequency power source 73 and the power source 83 for heat generation to start applying thermal energy after application of high-frequency power energy ends.

Application of thermal energy to a living tissue for more than a proper time period not only brings about no improvement in effectiveness but also has adverse effects, such as adherence of the living tissue to a treatment surface. For the reason, application of thermal energy needs to be ended at a proper time. Proper application end times, however, vary according to the type, size, and the like of a living tissue being treated. A user thus needs to monitor a treatment status and end application of thermal energy on the basis of experience and the like.

When a process of destroying cell membranes in a living tissue is completed through application of HF energy, switching from HF energy application mode to thermal energy application mode is performed. In thermal energy application mode, moisture is removed by further raising temperature of the living tissue, and a process of joining the living tissue is performed through hydrogen bonding.

Treatment is completed by stopping application of thermal energy when the joining process is appropriately ended. Since the control section 94 (the TH control section 84) automatically ends application of thermal energy in a proper time period on the basis of change in temperature, the treatment system 10 has good operability.

Figure 5:
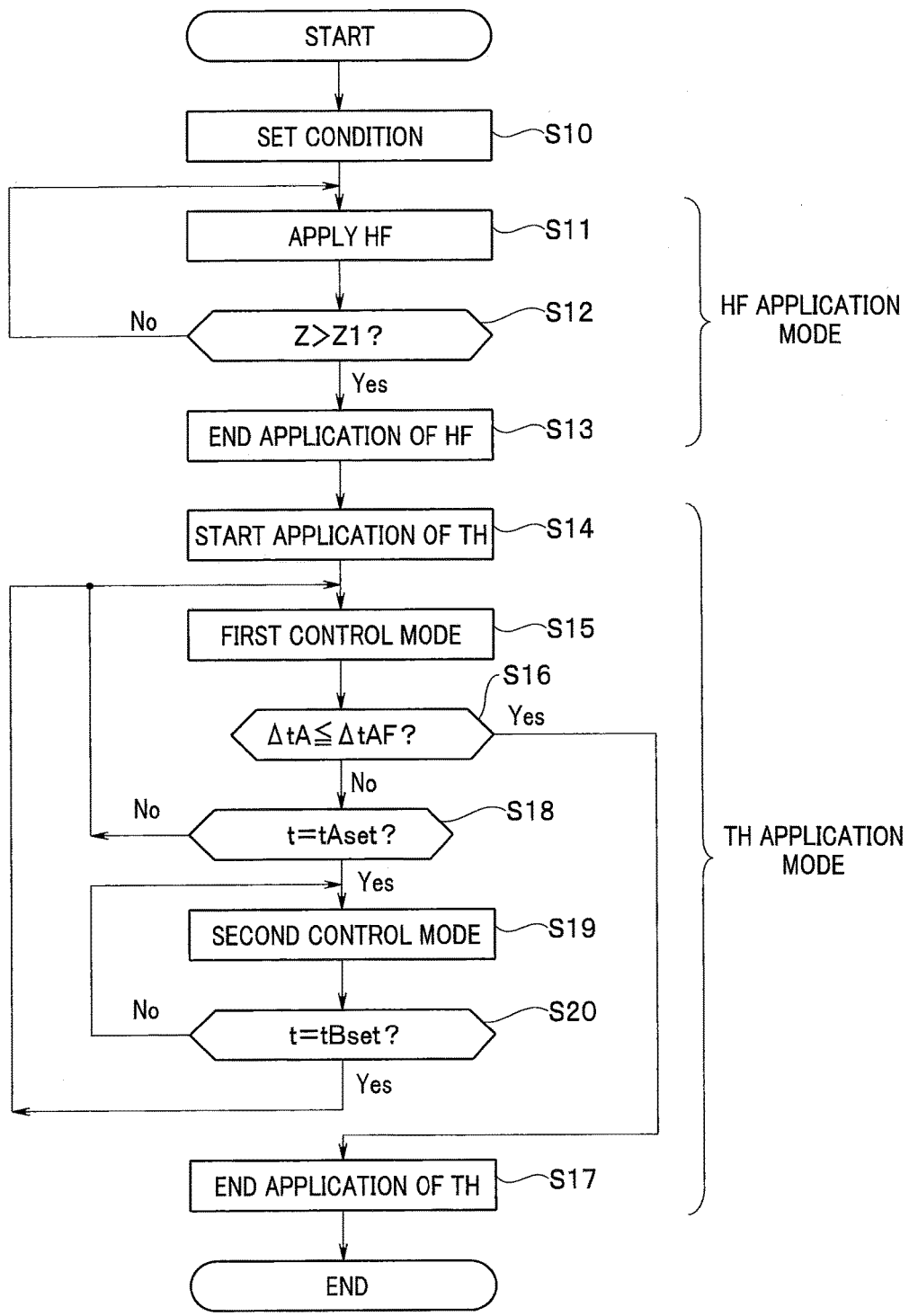
FIG. 5 is a flowchart for explaining a flow of processing of the treatment system according to the first embodiment.

A motion of the treatment system 10 will be described below in detail with reference to a flowchart shown in FIG. 5.

<Step S10>

A surgeon inputs and sets treatment conditions to the control section 94 by using the operation panels 76 and 86. Examples of the treatment conditions include setting power Pset (W) for HF energy application mode, a setting temperature Tset (° C.) for thermal energy application mode, and a threshold value Z1 (Ω) for an HF impedance Z for determining when to end HF energy application mode. Note that the treatment conditions will be described in detail later.

<Step S11>

The surgeon puts his or her fingers on the rings 33a and 33b of the handle portions 34a and 34b of the treatment instrument 11, operates the treatment instrument 11, and grasps a living tissue to be treated with the jaws 36a and 36b.

When the surgeon presses the pedal 13a of the foot switch 13 with a foot, application of HF energy to the living tissue between the electrodes 52a and 52b of the jaws 36a and 36b of the treatment instrument 11 starts. Note that the pedal 13a remains pressed during treatment. When the surgeon takes the foot off the pedal 13a, the power supply portion 12 forcibly stops outputting the energy.

HF outputted by the high-frequency power source 73 is controlled by constant power control to a predetermined setting power Pset (e.g., about 20 W to 150 W).

In HF energy application mode, Joule heat is generated to heat the living tissue itself. Dielectric breakdown, electric discharge, and the like arising from HF action destroy cell membranes in the living tissue. With the destruction of the cell membranes, released materials from the cell membranes are uniformed with extracellular components typified by collagen.

Figure 6:
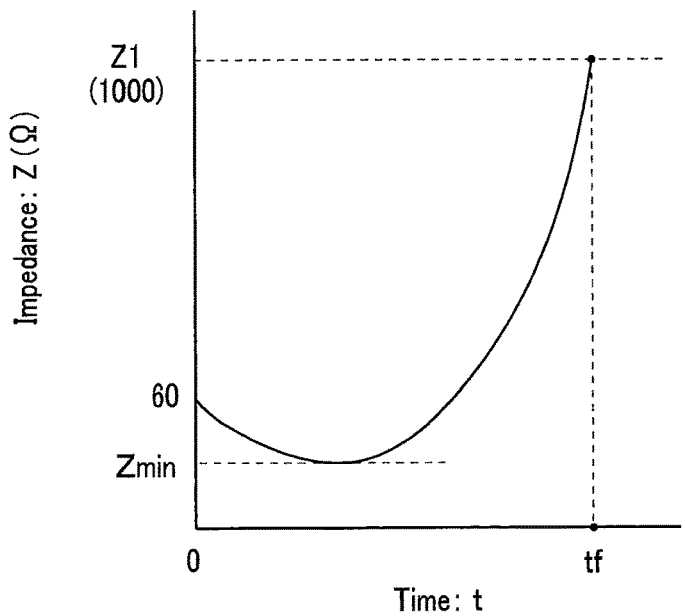
FIG. 6 is a graph showing change in impedance in high-frequency power application mode.

In HF energy application mode, the impedance Z for HF, i.e., the impedance Z in the grasped living tissue is calculated on the basis of HF information from the HF sensor 75. As shown in FIG. 6, the impedance Z is, for example, about 60Ω at the start of the HF energy application, decrease after the start to exhibit a minimum value Zmin, and increase after the exhibition.

<Step S12>

Since application of HF energy advances drying of the living tissue, the impedance Z for HF rises. Completion of the process of destroying cell membranes in the grasped living tissue is sensed on the basis of the impedance Z. That is, since when the destruction process is completed, substances in cell membranes are released no longer, rise in the impedance Z accelerates. Additionally, when the impedance Z is high, appropriate HF energy application is difficult.

For the reason, the control section 94 (the HF control section 74) determines, on the basis of a predetermined threshold value Z1, whether to end HF energy application mode.

The threshold value Z1 is, for example, about 10Ω to 1500Ω. Note that the surgeon need not set the threshold value Z1 if the threshold value Z1 is incorporated in advance in a program of the control section 94 (the HF control section 74). Alternatively, whether to end HF energy application mode may be determined by another method.

The HF control section 74 determines whether the impedance Z has exceeded the threshold value Z1 (e.g., 1000Ω). If the HF control section 74 determines that a value of the impedance Z is less than the threshold value Z1 (NO in S12), the HF control section 74 continues applying HF energy.

<Step S13>

On the other hand, if the HF control section 74 determines that the impedance Z has exceeded the threshold value Z1 (YES in S12), the HF control section 74 controls the high-frequency power source 73 so as to stop outputting HF.

<Step S14>

If the HF control section 74 determines that the impedance Z has become not less than the threshold value Z1, a signal is transmitted from the HF control section 74 of the HF unit 72 to the TH control section 84 of the TH unit 82 via the communication line 91. Switching from HF energy application mode to TH energy application mode is performed.

In TH energy application mode, by further raising a temperature T of the heater member 53, proteins in the living tissue are integrally denatured, and removal of moisture that is a hindrance to hydrogen bonding between proteins is performed.

In the treatment system 10, the TH control section 84 repeats, in TH energy application mode, a first control mode of performing constant temperature control (feedback control) such that the temperature of the heater member 53 reaches a first temperature TA and a second control mode of performing constant temperature control (feedback control) such that the heater member 53 reaches a second temperature TB which is lower than the first temperature TA.

<Step S15>

Figure 7:
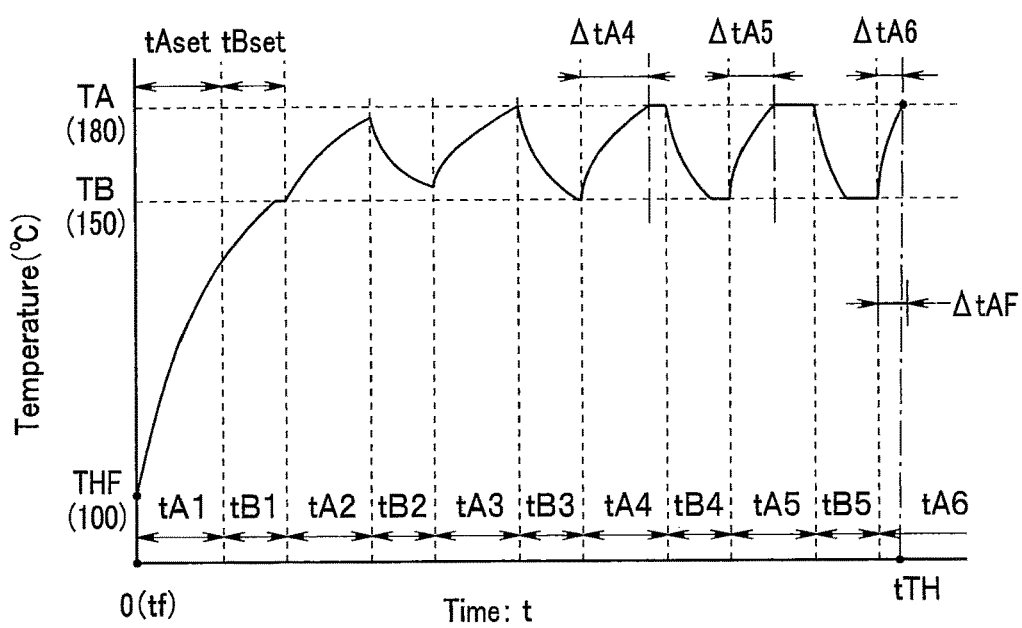
FIG. 7 is a graph showing change in temperature in power-for-heat-generation application mode in the treatment system according to the first embodiment.

Change in the temperature of the heater member 53 in a case where the first temperature TA and the second temperature TB are 180° C. and 150° C., respectively, in TH energy application mode is shown in FIG. 7.

A temperature THF of the heater member 53 when TH energy application mode starts, i.e., HF energy application mode ends (tf) is, for example, 100° C.

During the first control mode (tA1 to tA6), the TH control section 84 controls the power source 83 for heat generation such that the temperature of the heater member 53 reaches the first temperature TA.

<Step S16>

The TH control section 84 determines whether a time period ΔtA for the temperature of the heater member 53 to reach the first temperature TA is not more than a predetermined threshold time period (ΔtAF).

<Step S17>

If the time period ΔtA is not more than the predetermined threshold time period (ΔtAF) (YES in S16), i.e., at a time tTH, the control section 94 controls the power source 83 for heat generation so as to end application of thermal energy.

<Step S18>

If the time period ΔtA exceeds the predetermined threshold time period (ΔtAF) (NO in S15), the control section 94 continues application of thermal energy in a first control mode until a first control mode setting time period (tAset) is reached (NO in S18). That is, the processes from step S16 are repeated.

<Step S19>

When the first control mode setting time period (tAset) has elapsed (YES in S18), the TH control section 84 changes control mode to a second control mode (tB1 to tB5) of controlling the power source 83 for heat generation such that the temperature of the heater member 53 reaches the second temperature TB.

<Step S20>

The control section 94 continues application of thermal energy in the second control mode until a second control mode setting time period (tBset) is reached (NO in S20). That is, the processes from step S19 are repeated.

On the other hand, when the second control mode setting time period (tBset) has elapsed (YES in S20), the processes from step S15, i.e., the processes in the first control mode are performed again.

As described above, in the treatment system 10, the control section 94 controls the power source 83 for heat generation so as to end application of thermal energy by determining in step S16 whether the time period ΔtA for the temperature T of the heater member 53 to reach the first temperature TA is not more than the predetermined threshold time period (ΔtAF).

Referring to FIG. 7, in the first control mode (tA1) for a first time, the temperature T of the heater member 53 rises from the temperature THF (100° C.) at the HF energy application mode end time (t=0 (tf)) but does not arrive at the first temperature TA. In the subsequent second control mode (tB1) for a first time, the temperature T rises further and arrives at the second temperature TB.

In the first control mode (tA2), the temperature T rises from the second temperature TB and does not arrive at the first temperature TA. In the second control mode (tB2), since the temperature T in an initial stage is higher than the second temperature TB, the temperature T decreases. In the first control mode (tA3), the temperature T rises and arrives at the first temperature TA. After tA3, the temperature T decreases in the second control mode (tB3, tB4, and tB5) while the temperature T rises in the first control mode (tA4, tA5, and tA6).

As shown in FIG. 7, in the first control mode, the time period (ΔTA) for the temperature T to rise to arrive at the first temperature TA decreases in the order: ΔtA4, ΔtA5, and ΔtA6. This is because moisture in the grasped living tissue decreases by application of thermal energy, and thermal capacity becomes low. That is, a change in status of the living tissue due to proceeding of the treatment can be determined by the time period (ΔTA) to arrive at the first temperature TA.

The control section 94 controls the power source 83 for heat generation so as to end application of thermal energy by using the time period (ΔTA) to arrive at the first temperature TA as a temperature change parameter based on change in the temperature of the heater member 53 in the first control mode.

That is, the treatment system 10 repeats a first control mode of performing control such that the heater member 53 reaches the first temperature TA and a second control mode of performing control such that the heater member 53 becomes lower than the first temperature TA and ends application of thermal energy on the basis of the temperature change parameter based on change in the temperature of the heater member 53 in the first control mode.

The treatment system 10 can perform proper treatment by ending application of thermal energy when the time period (ΔTA) to arrive at the first temperature TA becomes not more than the predetermined threshold time period (ΔtAF), even if the type, size, initial moisture content, and the like of a living tissue being processed are different.

That is, the treatment system 10 and an actuation method for the treatment system 10 are capable of removing moisture from a living tissue and joining the living tissue through hydrogen bonding and then automatically completing treatment in an appropriate manner without applying excessive heat to the living tissue, even if the type and the like of the grasped living tissue are different. The treatment system 10 and the actuation method for the treatment system 10 are thus good in operability.

Note that the first temperature TA is set to a treatment temperature (e.g., 120° C. to 300° C.) and that the second temperature TB is set to, for example, 120° C. to 300° C. lower by 10° C. to 100° C. than the first temperature TA. If the second temperature TB is within the above-described range, detection accuracy for the time period (ΔTA) to arrive at the first temperature TA is high, and the treatment can be properly completed. The second control mode setting time period (tBset) is preferably shorter than the first control mode setting time period (tAset) in order to complete the process in a short time period.

Note that a rate (ΔT/Δt) of change in temperature in the first control mode may be used as the temperature change parameter instead of the time period (ΔTA) to arrive at the first temperature TA in the first control mode.

Alternatively, a time period to arrive at the second temperature TB in the second control mode or a rate (ΔT/Δt) of change in temperature in the second control mode may be used as the temperature change parameter.

Alternatively, the plurality of parameters described may be used in combination as the temperature change parameter. That is, as the temperature change parameter, at least one of a time period to arrive at a predetermined temperature and a rate of change in temperature can be used.

Second Embodiment

A treatment system 10A according to a second embodiment will be described. Since the treatment system 10A is similar to the treatment system 10, constituent elements having identical functions are denoted by identical reference numerals, and a description of the constituent elements will be omitted.

Figure 8:
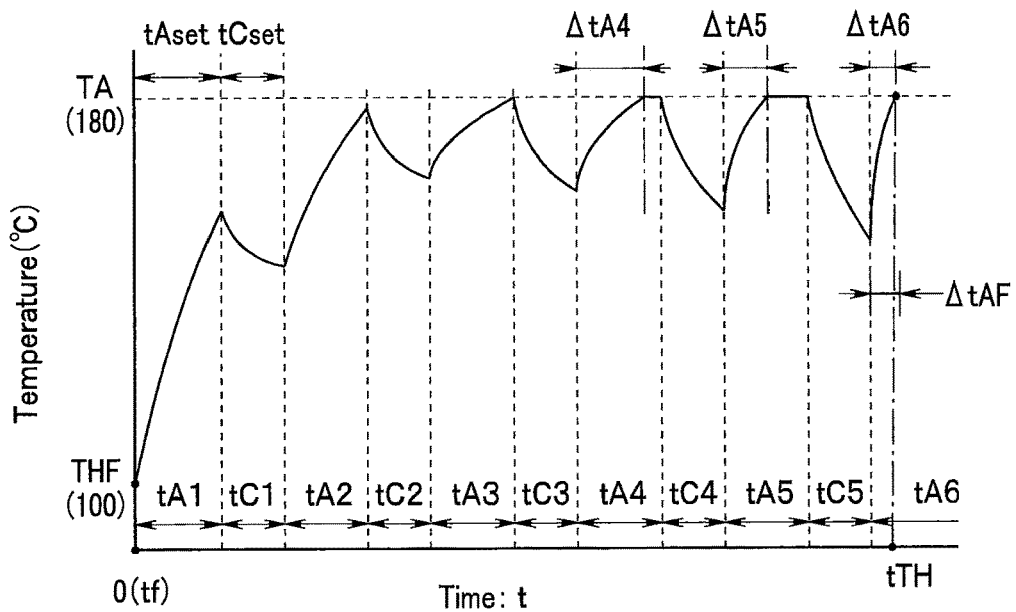
FIG. 8 is a graph showing change in temperature in power-for-heat-generation application mode in a treatment system according to a second embodiment.

As shown in FIG. 8, in the treatment system 10A, a TH control section 84 repeats, in TH energy application mode, a first control mode of performing control such that temperature of a heater member 53 reaches a first temperature TA and a second control mode of controlling a power source 83 for heat generation so as to suspend outputting power (TH) for heat generation such that the heater member 53 becomes lower than the first temperature TA.

A temperature T of the heater member 53 rises in the first control mode (tA1 to tA6) and decreases in the second control mode (tC1 to tC5).

The treatment system 10A uses, as a temperature change parameter based on change in the temperature of the heater member 53, a time period (ΔTA) to arrive at the first temperature TA or a rate (ΔT/Δt) of rise in temperature in the first control mode or a time period (ΔTX) to arrive at a predetermined temperature TX or a rate (ΔT/Δt) of decrease in temperature in the second control mode, like the treatment system 10. With the use, the treatment system 10A controls the power source 83 for heat generation so as to end application of thermal energy.

The treatment system 10A and an actuation method for the treatment system 10A have effects identical to effects of the treatment system 10 or the like. Additionally, the treatment system 10A and the actuation method easily control the power source 83 for heat generation.

Third Embodiment

A treatment system 10B according to a third embodiment will be described. Since the treatment system 10B is similar to the treatment system 10 or the like, constituent elements having identical functions are denoted by identical reference numerals, and a description of the constituent elements will be omitted.

Figure 9:
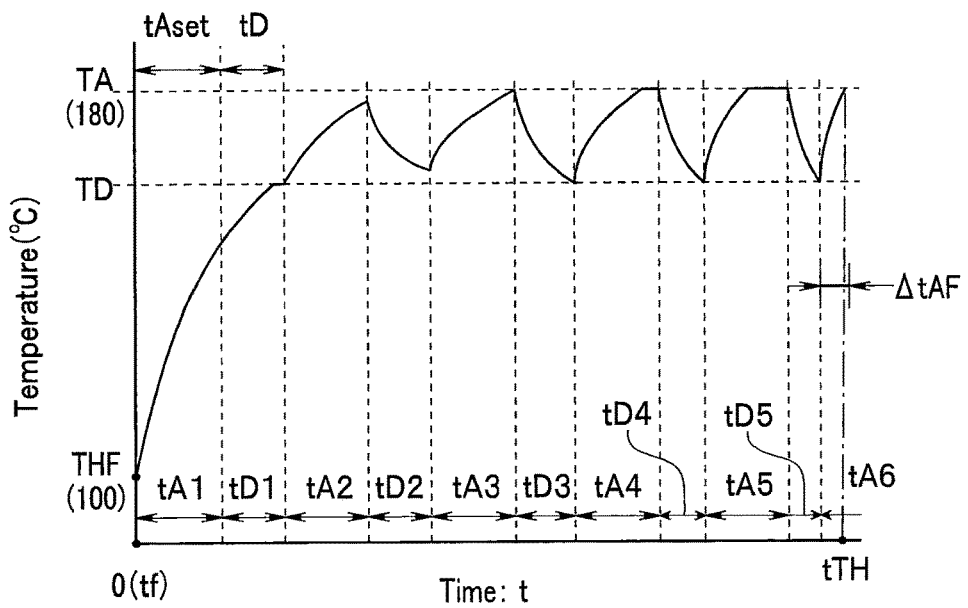
FIG. 9 is a graph showing change in temperature in power-for-heat-generation application mode in a treatment system according to a third embodiment.

As shown in FIG. 9, in the treatment system 10B, a TH control section 84 repeats, in TH energy application mode, a first control mode of performing control such that temperature of a heater member 53 reaches a first temperature TA and a second control mode of performing control such that the heater member 53 becomes lower than the first temperature TA, like the treatment systems 10 and 10A.

When the temperature of the heater member 53 reaches a predetermined second temperature TD in the second control mode, the treatment system 10B switches to the first control mode. For the reason, as the treatment proceeds, a time period (tD) for the second control mode decreases. That is, tD5<tD4<tD3, tD2 holds in FIG. 9. Note that the second temperature TD is determined under same conditions as conditions for the second temperature TB for the treatment system 10A.

The treatment system 10B controls a power source 83 for heat generation so as to end application of thermal energy by using, as a temperature change parameter based on change in the temperature of the heater member 53, a time period ($\Delta$TA) to arrive at the first temperature TA or a rate ($\Delta$T/$\Delta$t) of rise in temperature in the first control mode or a time period ($\Delta$TX) to arrive at a predetermined temperature TX or a rate ($\Delta$T/$\Delta$t) of decrease in temperature in the second control mode, like the treatment system 10. Alternatively, in the treatment system 10B, the time period (tD) for the second control mode may be used as the temperature change parameter.

The treatment system 10B and an actuation method for the treatment system 10B have effects identical to effects of the treatment system 10A or the like, and the time period (tD) for the second control mode, in which a small amount of thermal energy is applied, is short. A time period to treatment completion can thus be shortened.

Note that, in the treatment system 10A as well, output of power (TH) for heat generation may be suspended in the second control mode, like the treatment system 10B.

Fourth Embodiment

A treatment system 10C according to a fourth embodiment will be described. Since the treatment system 10C is similar to the treatment systems 10 to 10B, constituent elements having identical functions are denoted by identical reference numerals, and a description of the constituent elements will be omitted.

Figure 10:
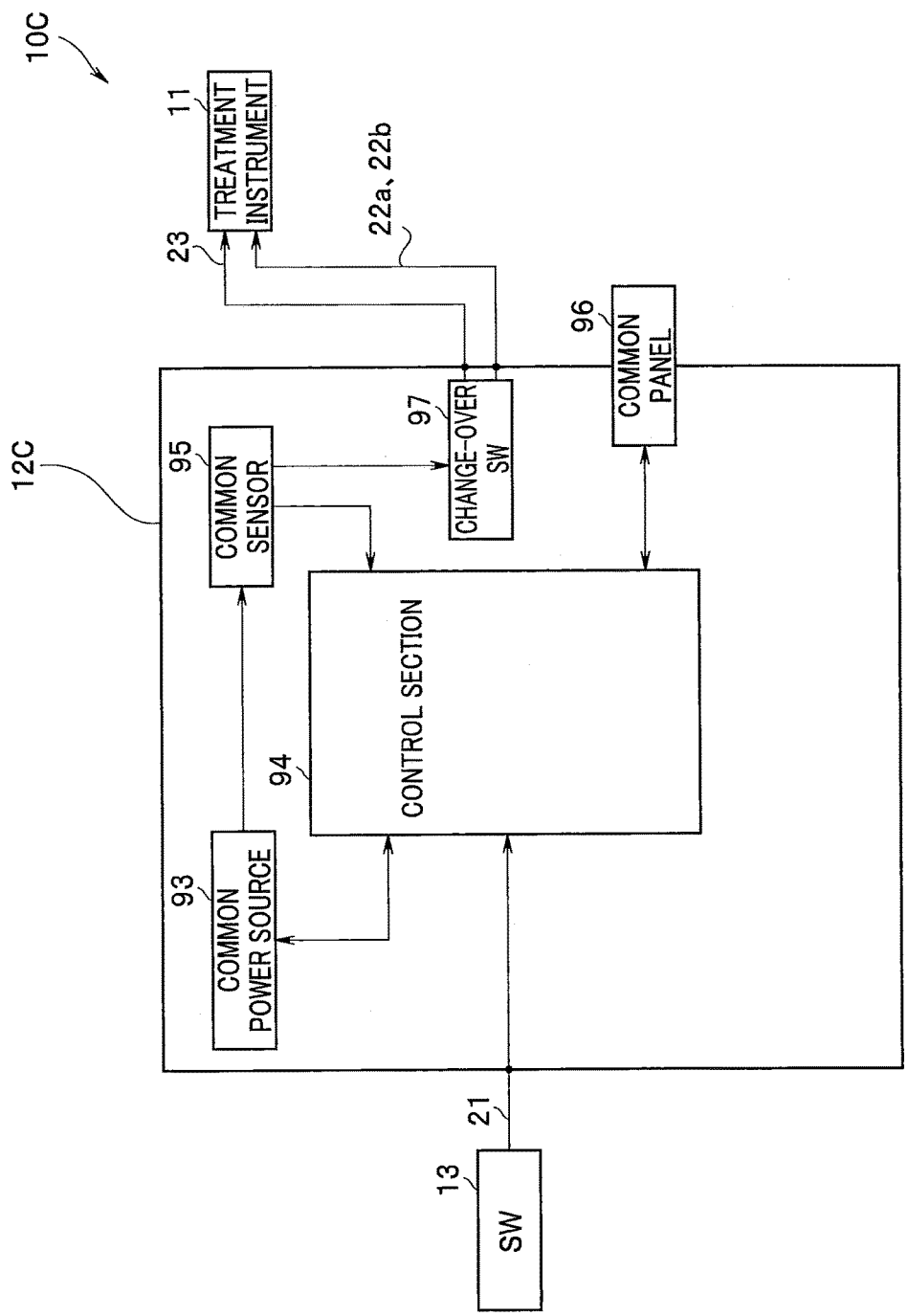
FIG. 10 is a configuration diagram of a treatment system according to a fourth embodiment.

As shown in FIG. 10, a power supply portion 12B of the treatment system 10C has a common power source 93 which has a high-frequency power source function and a power-source-for-heat-generation function and a change-over switch 97 which switches an output destination. The power supply portion 12B further has a common sensor 95 which has the function of an HF sensor 75 and the function of a TH sensor 85.

As already described, the high-frequency power source 73 and the power source 83 for heat generation do not simultaneously output power even in the treatment systems 10 to 10B according to the embodiment. For the reason, in the treatment system 10C, the one common power source 93 functions as a high-frequency power source or a power source for heat generation under control of a control section 94.

That is, in HF application mode, HF outputted by the common power source 93 is sent to HF lines 22a and 22b via the change-over switch 97. In TH application mode, TH outputted by the common power source 93 is sent to the TH line 23 via the change-over switch 97.

Note that the common sensor 95 functions as an HF sensor or a TH sensor and that a common panel 96 functions as an HF panel or a TH panel.

The treatment system 10C and an actuation method for the treatment system 10C have the same functions as functions of the treatment systems 10 to 10B and the like and are simple in configuration.

Note that, in a treatment system in which respective heater members are disposed at jaws 36a and 36b of a treatment instrument 11, respective power sources for heat generation may be controlled on the basis of temperatures of the heater members. Alternatively, control may be performed by one power source for heat generation on the basis of an average temperature of the two heater members.

Fifth Embodiment

A treatment system 10D according to a fifth embodiment will be described. Since the treatment system 10D is similar to the treatment system 10 or the like, constituent elements having identical functions are denoted by identical reference numerals, and a description of the constituent elements will be omitted.

Figure 11:
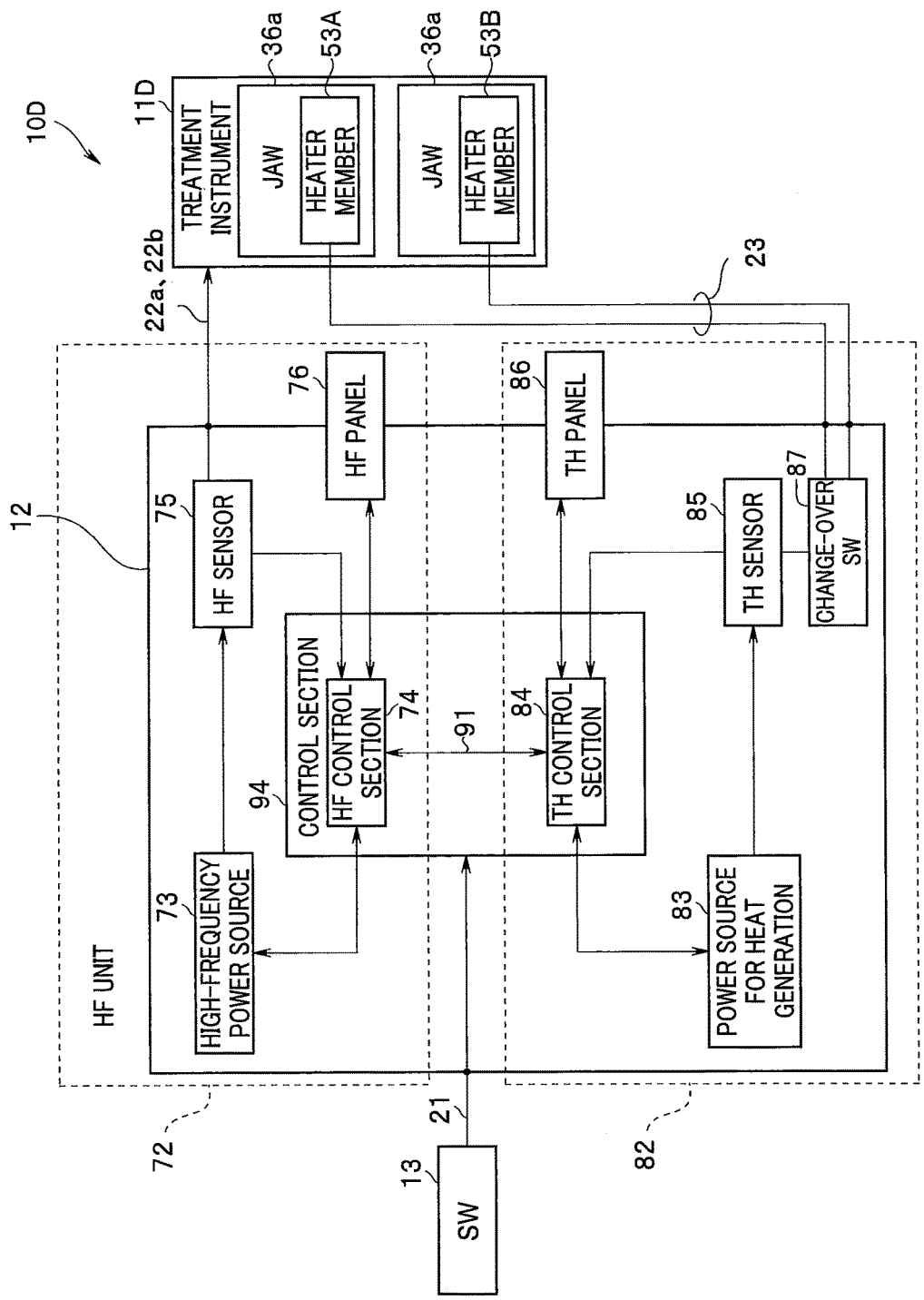
FIG. 11 is a configuration diagram of a treatment system according to a fifth embodiment.

As shown in FIG. 11, in the treatment system 10D, one pair of grasping members of a treatment instrument 11D is made up of a first grasping member (a jaw 36a) which has a first heating element (a heater member 53A) and a second grasping member (a jaw 36b) which has a second heating element (a heater member 53B). The treatment system 10D further includes a change-over switch 87 for supplying power (TH) for heat generation to the heater member 53A in the first control mode and to the heater member 53B in the second control mode.

Figure 12:
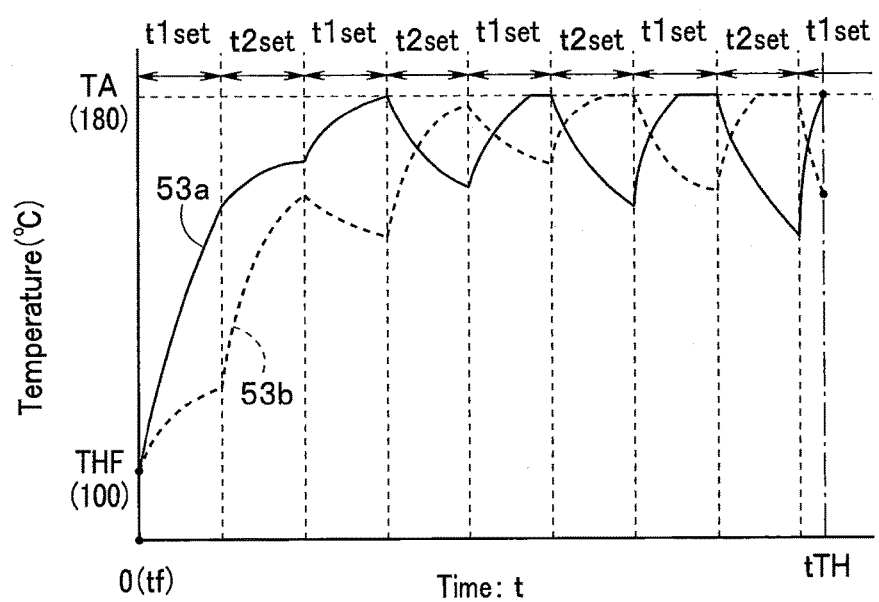
FIG. 12 is a graph showing change in temperature in power-for-heat-generation application mode in the treatment system according to the fifth embodiment.

As shown in FIG. 12, when TH energy application mode proceeds, temperature of the heater member 53A rises, and temperature of the heater member 53B declines, in the first control mode (t1set). On the other hand, the temperature of the heater member 53B rises, and the temperature of the heater member 53A declines, in the second control mode (t2set).

A control section 94 ends application of thermal energy on the basis of a temperature change parameter for the heater member 53A or 53b in the second control mode, in addition to a temperature change parameter of the heater member 53A or 53b in the first control mode.

As already described, a time period ($\Delta$tA) for a temperature T of the heater member 53A or 53B to rise to a first temperature TA, a rate ($\Delta$T/$\Delta$t) of rise in temperature, or the like can be used as the temperature change parameter. Additionally, a time period for the temperature T of the heater member 53A or 53b to decrease to a predetermined temperature, a rate of decrease, or the like can be used as the temperature change parameter.

The treatment system 10D and an actuation method for the treatment system 10D have effects identical to effects of the treatment system 10 or the like. Additionally, since TH is continuously outputted from a power source for heat generation to the treatment instrument, a treatment time period is short. In addition, since a living tissue is heated from two sides, heating unevenness is unlikely to occur.

Note that a common power source 93 which has a high-frequency power source function and a power-source-for-heat-generation function can also be used in the treatment system 10D, like the treatment system 10C.

As described above, a control method, i.e., an actuation method for a treatment system includes a step of setting a treatment condition for the treatment system including one pair of grasping members which apply high-frequency power energy and thermal energy to a grasped living tissue, a high-frequency power source which outputs high-frequency power for applying the high-frequency power energy, and a power source for heat generation which outputs power for heat generation for applying the thermal energy, a step of controlling the high-frequency power source on the basis of the treatment condition and applying the high-frequency power energy to the living tissue, a step of acquiring a parameter, on the basis of change in temperature of the heating element in a first control mode of performing control such that the heating element reaches a first temperature or a second control mode of performing control such that the heating element becomes lower than the first temperature, during application of the thermal energy by repeating the first control mode and the second control mode on the basis of the treatment condition after application of the high-frequency power energy is ended on the basis of the treatment condition, and a step of ending application of the thermal energy according to the temperature change parameter.

The present invention is not limited to the above-described embodiments and the like. Various changes, modifications, and the like can be made without departing from the scope of the present invention.

What is claimed is:

1. A treatment system comprising:
    a power source;
    a controller configured to control the power source;
    a treatment instrument including a pair of grasping members configured to grasp a living tissue, and
    a heating element disposed on at least one of the pair of the grasping members, the heating element being electrically connected to the power source and configured to generate heat with power outputted from the power source;
    wherein the controller is configured to:
        repeatedly perform a control in a first control mode for controlling an output of the power so as to increase a temperature of the heating element to a first temperature and to keep the temperature of the heating element at the first temperature, and a control in a second control mode for controlling the output of the power such that the temperature of the heating element decreases,
        stop the output of the power based on at least one of a first result of a comparison between a time period for the temperature during one period in the first control mode or during one period in the second control mode of the heating element to reach a predetermined temperature and a preset threshold time period and a second result of a comparison between a rate of change in the temperature of the heating element during one period in the first control mode or during one period in the second control mode and a preset threshold rate; and
        control the output of the power such that the temperature of the heating element is kept constant at a second temperature lower than the first temperature in the second control mode.

2. The treatment system according to claim 1, wherein the controller is further configured to control the output of the power based on a time period for the temperature of the heating element to reach the first temperature or a rate of rise in the temperature of the heating element in a process in which the temperature of the heating element rises to the first temperature.

3. The treatment system according to claim 1, wherein the controller is further configured to control the output of the power based on a time period for the temperature of the heating element to reach the second temperature or a rate of decrease in the temperature of the heating element in a process in which the temperature of the heating element decreases to the second temperature.

4. The treatment system according to claim 1, wherein the controller is further configured to repeatedly perform the control in the first control mode and the control in the second control mode by switching the first control mode and the second control mode based on a preset setting time period.

5. The treatment system according to claim 1, wherein the controller is further configured to repeatedly perform mode switching so as to switch to the second control mode after performing the control in the first control mode for a preset first setting time period and switch to the first control mode after performing the control in the second control mode for a preset second setting time period, and controls the output of the power based on a time period for the temperature of the heating element to reach the first temperature or a rate of rise in the temperature of the heating element in a process in which the temperature of the heating element rises to the first temperature.

6. The treatment system according to claim 5, wherein the second setting time period is shorter than the first setting time period.

7. The treatment system according to claim 1, wherein the controller is further configured to repeatedly perform mode switching so as to switch to the second control mode after performing the control in the first control mode for a preset first setting time period and switch to the first control mode after performing the control in the second control mode for a preset second setting time period, and controls the output of the power based on a time period for the temperature of the heating element to reach the second temperature or a rate of decrease in the temperature of the heating element in a process in which the temperature of the heating element decreases to the second temperature.

8. The treatment system according to claim 7, wherein the second setting time period is shorter than the first setting time period.

9. The treatment system according to claim 1, wherein
    the controller is further configured to repeatedly perform the control in the first control mode and the control in the second control mode by switching the control mode to the first control mode when the temperature of the heating element reaches the second temperature in the second control mode.

10. The treatment system according to claim 9, wherein the controller is further configured to perform the control in the first control mode for a preset setting time period.

11. The treatment system according to claim 1, wherein the controller is further configured to control the output of the power such that the temperature of the heating element reaches the first temperature in the first control mode and perform the control to stop the output of the power in the second control mode.

12. The treatment system according to claim 11, wherein the controller is further configured to control the output of the power based on a time period for the temperature of the heating element to reach the first temperature or a rate of rise in the temperature of the heating element in a process in which the temperature of the heating element rises to the first temperature.

13. The treatment system according to claim 11, wherein the controller is further configured to repeatedly perform the control in the first control mode and the control in the second control mode by switching the first control mode and the second control mode based on a preset setting time period, and controls the output of the power based on a time period for the temperature of the heating element to reach the first temperature or a rate of rise in the temperature of the heating element in a process in which the temperature of the heating element rises to the first temperature.

* * * * *